Figure 1:
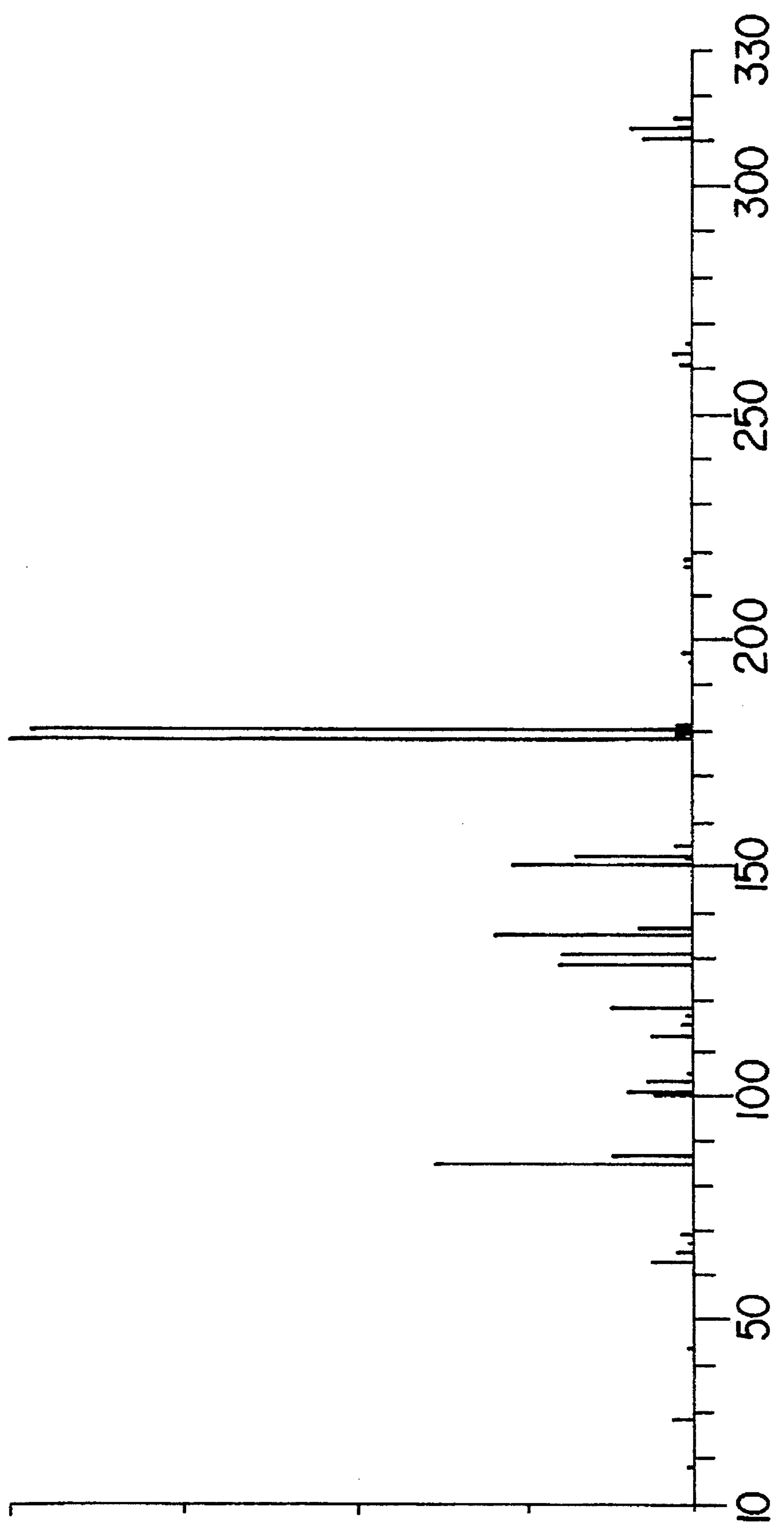

US005457242A

United States Patent [19]

Calini et al.

[11] Patent Number: 5,457,242

[45] Date of Patent: Oct. 10, 1995

[54] 2-BROMO,1',2'-DICHLOROPERFLUORO DIETHYL ETHER AND PROCESS FOR PREPARING SAME

[75] Inventors: Pierangelo Calini; Guglielmo Gregorio, both of Milan; Giorgio Guglielmo, Venice, all of Italy

[73] Assignee: Ausimont S.r.l., Milan, Italy

[21] Appl. No.: 148,545

[22] Filed: Nov. 8, 1993

Related U.S. Application Data

[63] Continuation of Ser. No. 45,386, Apr. 13, 1993, abandoned, which is a continuation-in-part of Ser. No. 796,879, Nov. 25, 1991, abandoned, which is a continuation of Ser. No. 649,122, Jan. 28, 1991, abandoned, which is a continuation of Ser. No. 380,679, Jul. 14, 1989, abandoned, which is a continuation of Ser. No. 119,100, Nov. 10, 1987, abandoned.

[30] Foreign Application Priority Data

Nov. 14, 1986 [IT] Italy ..................................... 22348/86

[51] Int. Cl.[6] .................................................. C07C 41/06

[52] U.S. Cl. ............................................................ 568/684

[58] Field of Search ............................................. 568/684

[56] References Cited

U.S. PATENT DOCUMENTS 4,577,044 3/1986 Campbell et al. .

FOREIGN PATENT DOCUMENTS

| | | | |
|---|---|---|---|
| 0267626 | 5/1986 | European Pat. Off. | 568/684 |
| 0201871 | 11/1986 | European Pat. Off. | 568/684 |
| 0269933 | 6/1988 | European Pat. Off. | 568/684 |
| 2148286 | 5/1985 | United Kingdom | 568/684 |

*Primary Examiner*—Johann Richter
*Assistant Examiner*—John Peabody
*Attorney, Agent, or Firm*—Morgan & Finnegan

[57] ABSTRACT

A process for preparing the novel compound 2-bromo, 1', 2'-dichloroperfluoro diethyl ether of formula:

BrCFhd 2—$CF_2$—O—CFCl—$CF_2$Cl where $BrCF_2$—$CF_2$ OF is reacted with the olefin CFCl═CFCl, with bromohypofluorite being introduced into the reaction mixture in the form of a solution in an inert solvent based on chlorofluorohydrocarbon.

5 Claims, 1 Drawing Sheet

2-BROMO,1',2'-DICHLOROPERFLUORO DIETHYL ETHER AND PROCESS FOR PREPARING SAME

This is a continuation divisional of application Serial No. 08/045,386 filed April 13, 1993 now abandoned which is a continuation-in-part of 07/796,879, filed Nov. 25, 1991, now abandoned, which is a continuation application of 07/649,122, filed Jan. 28, 1991, now abandoned; which is a continuation of 07/380,679 filed Jul. 14, 1989, now abandoned, which is a continuation of 07/119,100, file Nov. 10, 1987, now abandoned, all of which are incorporated herein by reference.

FIELD OF THE INVENTION

An object of the present invention is the synthesis of a new compound having the structure of a substituted halogen ether of formula:

$$BrCF_2—CF_2—O—CFCl—CF_2Cl \quad (I)$$

This compound is of particular importance as a starting product for the synthesis of bromofluorovinylether, for dechlorination in the presence of metals as disclosed in the U.S. Pat. No. 4,937,391, the subject matter of which is incorporated herein by reference. The bromofluorovinylether is a comonomer of particular interest for the preparation of fluoroelastomers vulcanizable with peroxides.

BACKGROUND OF THE INVENTION

It is known how to prepare fluorinated ethers by addition of hypofluorite to fluorochloro-olefins, as is described in Italian patent application No. 20781 A/85 in the name of the Applicant hereof. This kind of reaction is generally conducted under strictly controlled conditions, maintaining the temperature at very low values (from −50° to +50° C.), as hypofluorite decomposition reactions can easily occur.

Furthermore, it should be taken into account that the yields can vary in an unforeseeable manner depending on the selected olefin and hypofluorite owing to other secondary reactions.

In particular, the reaction of 2-bromoperfluoroethylhypofluorite with difluoro-dichloroethylene was not known.

The preparation of hypofluorite of formula $BrCF_2—CF_2OF$ is disclosed in patent application No. 21632 A/86, fluorine is directly reacted with $BrCF_2—COF$ on cesium fluoride as a catalyst, in the presence of nitrogen as a diluent to produce $BrCF_2—CF_2OF$.

Hypofluorite is an unstable compound and easily leads to β scission reactions; it was observed that by reacting the gas stream of $N_2$-diluted hypofluorite with the olefin dissolved in a solvent, even at low temperature, the product did not form.

THE PRESENT INVENTION

It has unexpectedly been found that the $BrCF_2—CF_2—O—CFCl—CF_2Cl$ adduct is obtained with high yields when the reaction is conducted by condensing the gas stream flowing from the hypofluorite synthesis reactor, by means of cooling, and addition, in equicurrent, of a proper fluorinated solvent, which is inert under the reaction conditions, and by feeding the resulting solution into the reactor which contains a CFCl=CFCl solution intensely stirred in an identical or analogous fluorine-stable solvent. It is advisable to operate in such manner in order to always have an excess of olefin with respect to hypofluorite.

The reaction product is distilled off from the solvent and the by-products, and it is recovered as a fraction having a boiling point of 100°–110° C. and characterized by mass spectrometry.

The process for preparing the claimed compound utilizes, as a reagent, gaseous $BrCF_2—CF_2OF$ in the admixture with an inert gas, preferably nitrogen, at a concentration of from 2 to 15% in the gaseous mixture, these being the best conditions for the synthesis of the same hypofluorite.

The solvent which makes possible the condensation of hypofluorite can be admixed with the gaseous stream either as a liquid or as a gas condensable at the temperature at which the addition takes place.

Suitable solvents are the chlorofluorohydrocarbons used as freezing fluids and commercially known under the tradename ALGOFRENE®, FREON®, etc., and in particular $CF_2Cl_2$, $CF_2Cl—CF_2Cl$.

The reaction temperature ranges from −40° to −150° C. It is apparent that at the lowest temperature only a few solvents, in particular $CF_2Cl_2$, are suited to the synthesis. The reaction is very quick and, by consequence, the olefin can also be continuously fed, slightly in excess with respect to the stoichiometric amount, to the reactor in which the addition occurs.

EXAMPLES

The following examples are given to illustrate the present invention.

EXAMPLE 1

0.7N l/h of $BrCF_2COF$ and 0.7N l/h of fluorine diluted in 30N l/h of helium were fed to an AISI 316 reactor containing 600 g of a catalyst containing 8% cesium fluoride based on copper and thermoregulated at a temperature of 25° C.

The gaseous stream flowing from the reactor, consisting of $BrCF_2—CF_2OF$ and inert was mixed with a flow of 7N l/h of $CF_2Cl_2$ and conveyed into a cooling coil maintained at a temperature of −78° C. in order to cause the condensation of the mixture of hypofluorite and $CF_2Cl_2$.

The liquid mixture so obtained was dropped into an intensely stirred flask containing 29 g of CFCl=CFCl (about 0.22 moles) dissolved in 330 g of $CF_2Cl_2$ and maintained, by means of a cooling bath, at a temperature of −78° C.

It was operated for 4 hours, during which 0.1 moles of $BrCF_2—CF_2OF$ were fed.

The resulting reaction mixture was allowed to slowly evaporate and the residue, analyzed by gas chromatography associated with mass spectrography, revealed the presence of a product, which exhibited a mass spectrum (FIG. 1) indicative of the structure for $BrCF_2—CF_2—O—CFCl—CF_2Cl$ In fact, among the fragmentations of a compound of formula $BrCF_2—CF_2—O—CFCl—CF_2Cl$ the following are expected:

a) loss of a chlorine, in the alpha position with respect to oxygen, which gives rise to mass fragments 311, 313, 315 respectively (FIG. 1). The relative intensities of the peaks observed in the mass spectrum are in a ratio corresponding to the natural isotopic abundance of the remaining chlorine atom or bromine atom;

b) loss of the $BrCF_2—CF_2—O—$ with formation of fragment —$CFCl$—$CF_2Cl$. The mass of the latter corresponds with mass fragment 151 and is present in the mass spectrum along with the signals of mass fragments 153 and 155. The relative intensities are in a ratio corresponding to the natural isotopic abundance of chlorine.

The illustrated mass spectrum is therefore to be considered as being in accordance with the proposed structure. By distillation of the raw reaction product, unreacted olefin was recovered and a fraction having a boiling point of 100°–110° C. was then isolated, corresponded to the claimed product because it was in accordance with the mass spectrum. In order to confirm the structure of the claimed product, it has been proved that the same product was obtained by reaction of chlorine with $BrCF_3$—$CF_2$—O—CF=$CF_2$. The yield was 30% with respect to the fed $CF_2Br$—COF.

EXAMPLE 2 (comparative test)

The test of Example 1 was repeated, with the exception that the gaseous hypofluorite stream was made to bubble into a flask containing CFCl=CFCl in $CFCl_2$—$CF_3$, at a concentration equal to 20% by volume and maintained at a temperature of −78° C.

On analysis, the reaction mixture did not reveal the presence of $BrCF_2$—$CF_2$—O—CFCl—$CF_2Cl$.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above-references are hereby incorporated by reference.

What we claim is:

1. A process for preparing 2-bromo-1',2'-dichloroperfluoro diethylether $BrCF_2$—$CF_2$—O—$CFClCF_2Cl$, comprising the steps of:

a) mixing a gaseous stream of $BrCF_2$—$CF_2OF$ in an inert gas with a gaseous stream of a chlorofluorohydrocarbon;

b) condensing the obtained gaseous mixture by cooling;

c) feeding the condensed solution into a reactor containing a solution of CFCl═CFCl and said chlorofluorohydrocarbon, wherein said CFCl═CFCl is present in stoichiometric excess relative to said $BrCF_2$—$CF_2OF$;

d) reacting said $BrCF_2$—$CF_2OF$ with said excess CFCl═CFCl under stirring at a temperature of from −40° to −150° C.

2. The process according to claim 1, wherein the reaction of step (d) is carried out at −78° C.

3. The process according claim 1, wherein the inert gas is selected from nitrogen and helium.

4. The process according claim 1, wherein the chlorofluorohydrocarbon is selected from $CF_2Cl$—$CF_2Cl$ and $CF_2Cl_2$.

5. The process according to claim 1, wherein the molar ratio between CFCl═CFCl and $BrCF_2CF_2OF$ is equal to about 2.2.

* * * * *